(12) United States Patent
Zhang et al.

(10) Patent No.: US 9,138,449 B2
(45) Date of Patent: Sep. 22, 2015

(54) MEDICINAL COMPOSITION FOR LIVER DISEASES

(75) Inventors: Ning Zhang, Shanghai (CN); Cheng Rong Wang, Shanghai (CN); Ping Liu, Shanghai (CN); Hua Shi Bian, Shanghai (CN); Jian Hua Zhang, Shanghai (CN); Xiu Rong Yuan, Shanghai (CN); Cheng Hai Liu, Shanghai (CN); Yao Wang Jin, Shanghai (CN); Hai Bo Ping, Shanghai (CN)

(73) Assignees: Shanghai Sundise Chinese Medicine Technology Development Co., Ltd., Shanghai (CN); Shanghai Huanghai Pharmaceutical Co., Ltd., Shanghai (CN)

( * ) Notice: Subject to any disclaimer, the term of this patent is extended or adjusted under 35 U.S.C. 154(b) by 1398 days.

(21) Appl. No.: 11/435,084

(22) Filed: May 15, 2006

(65) Prior Publication Data
US 2007/0160626 A1    Jul. 12, 2007

(51) Int. Cl.
| A61K 36/068 | (2006.01) |
| A61K 36/15 | (2006.01) |
| A61K 36/23 | (2006.01) |
| A61K 36/424 | (2006.01) |
| A61K 36/537 | (2006.01) |
| A61K 36/575 | (2006.01) |
| A61K 36/736 | (2006.01) |
| A61K 36/79 | (2006.01) |

(52) U.S. Cl.
CPC ............... *A61K 36/23* (2013.01); *A61K 36/068* (2013.01); *A61K 36/15* (2013.01); *A61K 36/424* (2013.01); *A61K 36/537* (2013.01); *A61K 36/575* (2013.01); *A61K 36/79* (2013.01)

(58) Field of Classification Search
CPC ..... A61K 36/068; A61K 36/15; A61K 36/23; A61K 36/424; A61K 36/537; A61K 36/575; A61K 36/736; A61K 36/79; A61K 2300/00
See application file for complete search history.

(56) References Cited

FOREIGN PATENT DOCUMENTS

| CN | 1243743 A | * | 2/2000 |
| CN | 1456348 |   | 11/2003 |
| CN | 1460517 A | * | 12/2003 |
| CN | 1788764 |   | 6/2006 |

OTHER PUBLICATIONS

Shanthi Wasser, Jean May Sian Ho, Hui Kheng Ang and Carolyn Eng Looi Tan, "*Salvia miltiorrhiza* reduces experimentally-induced hepatic fibrosis in rats", Journal of Hepatology, 1998, 29, 760-771.*
CN 1456348 machine-generated translation.*
CN 1788764 machine-generated translation.*
Chen-Kai Chang, Ku-Shang Chang, Yi-Chen Lin, Sin-Yie Liu & Chien-Yuan Chen, "Hairy root cultures of *Gynostemma pentaphyllum* (Thunb.) Makino: a promising approach for the production of gypenosides as an alternative of ginseng saponins", Biotechnology Letters (2005) 27: 1165-1169.*
Stephen Kwok-Fan Cheung, "Anti-Fibrogenic Effect of Traditional Chinese Medicine 319 Recipe", Thesis for the Degree of Master of Philosophy, 2007, The University of Hong Kong.*
Tan et al., "Influence of Health-Supporting and Stasis-Resolving Decoction on Gelatin Enzyme,TIMP-2 and Astrocyte Apoptosis in Rat Liver" ACTA Universitatis Traditions Medicalis Sinensis Pharmacologiaeque Shanghai, 2003, 17(4), pp. 216-219, 2003, 17 (4)).

* cited by examiner

*Primary Examiner* — Sue Liu
*Assistant Examiner* — Nathan W Schlientz
(74) *Attorney, Agent, or Firm* — Squire Patton Boggs (US) LLP

(57) ABSTRACT

The invention provides a composition containing extracts from *salvia miltiorrhiza* bunge, *gynostemma pentaphyllum mak*, Chinese magnoliavine, *cordyceps* extract piece, pollen pini, and semen persicae and methods of and using the same.

18 Claims, 4 Drawing Sheets

Normal Group

Model Group

Preparation I

Preparation II

Vitamin E

Normal Group

Model Group

Preparation I

Preparation II

Vitamin E

Normal Group

Model Group

Preparation I

Preparation II

NAC Group

Normal Group

Model Group

Preparation I

Preparation II

NAC Group

MEDICINAL COMPOSITION FOR LIVER DISEASES

PRIORITY DATA

This application claims priority of Chinese patent application number 200610023308.3, filed Jan. 12, 2006, the disclosure of which is incorporated herein by reference.

TECHNOLOGICAL FIELD

The present invention generally relates to a Chinese medicinal composition for treat, preventing or ameliorating a liver disease.

BACKGROUND OF THE INVENTION

Liver fibrosis is a pathological process through which chronic liver disease such as chronic hepatitis B, alcoholic liver disease, fatty liver etc. developed into liver cirrhosis. The formation and development of liver fibrosis crucially affect prognosis and outcome of chronic liver diseases, and treatment of liver fibrosis is the one of the two most challenging tasks in the clinical treatment of chronic liver diseases, the other being etiologic treatment. The statistics data shown that there are 1.5 billion hepatitis B infectors in our country, among which there are thirty million patients suffering from chronic hepatitis Bs. The hazard of chronic hepatitis is well documented, which could infect other people on one hand, on the other it could develop into liver fibrosis.

It is observed that 65 wt % of patients with slight hepatitis B have liver fibrosis, but 100 wt % in moderate and severe patients. Over 30 wt % of chronic hepatitis patients will inevitably develop into liver cirrhosis. Nowadays in China, more than 10 wt % of population suffers from fatty liver, in which 50 wt % patients are due to obesity and 57.5 wt % due to alcohol. In addition the incidence of alcoholic liver diseases will increase as the living standard improves. No matter alcoholic or non alcoholic fatty liver diseases, the incidence of liver fibrosis has reached 25 wt % of patient population, 1.5 wt %~8 wt % of which will become liver cirrhosis.

Liver fibrosis is a active repairing reaction to chronic damage, which characters with extracellular matrix (ECM) overproduction and deposition and the morphological features of hepatic sinusoid capillarization and lobule fibrosis. Almost all the chronic liver diseases, including chronic hepatitis B and C, chronic schistosomiasis, chronic alcoholic and drug damage, autoimmunity liver diseases have the pathological feature of liver fibrosis. These diseases would develop into liver fibrosis as the fibrosis continues, accompanying by liver dysfunction and portal hypertension, which severely affect patients' health and threaten their life at last.

Modern medicine researches indicated that hepatic stellate cell activation is the cellular basis of liver fibrogenesis, while imbalance of ECM metabolism including collagens that character as its production exceeding degradation is the biochemical foundation of fibrosis. It is now recognized that liver fibrosis is reversible, and, to some degree, liver cirrhosis can also be reversed. Therefore anti-fibrosis treatment is not only important but feasible and of clinical significance.

An existent technology, which is a capsule preparation (China patent: 99113887.2), made from *salvia miltiorrhiza, pruni persicae, cordyceps* mycelial threads and so on, can be effective against liver fibrosis due to chronic hepatitis B. However, this preparation has some shortcomings, including the shortcomings in dosage, moisture absorption, stimulation to stomach and intestine and etc. And these drawbacks would affect the preparation's stability and pharmacodynamic function.

SUMMARY OF THE INVENTION

The present invention provides a composition comprising extracts from traditional Chinese medicine to treat, prevent, or ameliorate liver diseases. In some embodiments, the composition described herein include an extract from *salvia miltiorrhiza* bunge; an extract from *cordyceps* extract piece; an extract from semen persicae; and an extract from at least one of *gynostemma pentaphyllum mak*, Chinese magnoliavine and pollen pini. In some embodiments, the extract from *salvia miltiorrhiza* bunge can have a percentage in the range between about 25 and about 40 wt %.

In some embodiments, the composition described herein comprises extracts from herbs for treating, preventing or ameliorating chronic hepatitis and liver fibrosis. In some embodiments, the invention provides a pharmaceutical formulation, which can be tablets, capsules, granules, dispersible tablets, sustained-release tablets, dropping pills or oral solutions.

The present invention also provides a method of preparing the composition described herein and a method of using the composition for treating, preventing, or ameliorating a liver condition.

BRIEF DESCRIPTION OF THE DRAWINGS

In FIG. 2, liver tissue were stained with Sirius red, there were fewer collagens deposition only in the portal and central vein area in the normal group. In the control group, collagen accumulated obviously and formed the fibrous septa along the degenerated hepatocytes. The model rats prevented with Fezheng Huayu Preps and Vitamin E had much better conditions of hepatic inflammation compared to the controls.

DETAILED DESCRIPTION OF THE INVENTION

Figure 1:
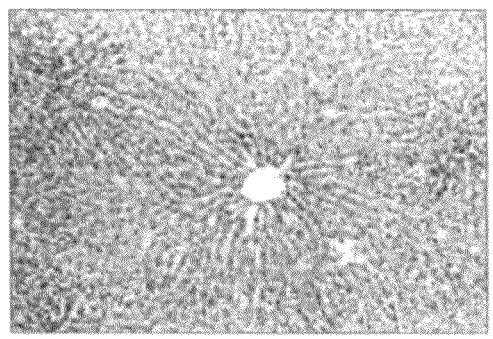
FIG. 1 shows the liver tissues stained with HE in liver fibrotic rats induced by $CCl_4$ as the normal group, model Control group, Fuzheng Huayu Preparation (Prep) I, Fuzheng Huayu Prep II, and Vitamin E group, respectively. In the figure, liver tissues were stained with HE. In the normal group, hepatic lobule structure keeps intact, and hepatocytes had no degeneration and necrosis. In the model control, mass of hepatocytes became necrotic and hydropic degenerated, the portal area widened, and a lot of inflammatory cells including monocytes infiltrated in the portal area and necrotic area, the hepatic lobule structure were distorted. The model rats prevented with Fezheng Huayu Preps and Vitamin E had much better conditions of hepatic inflammation compared to the controls.
Figure 1:
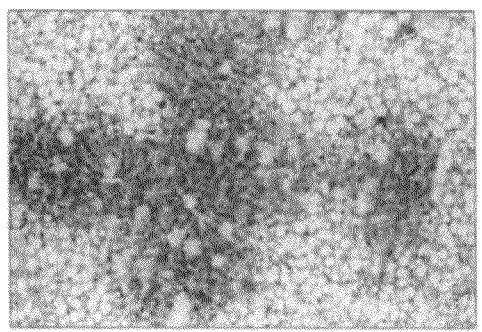
Figure 1:
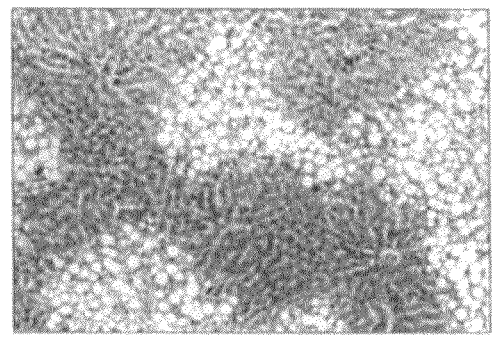
Figure 1:
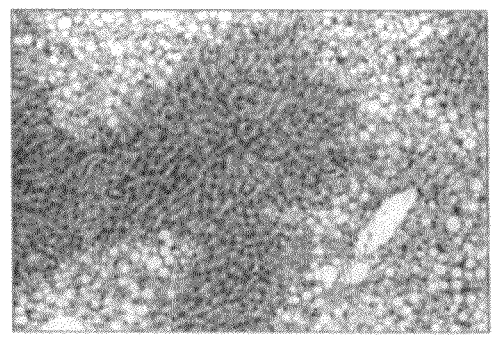
Figure 1:
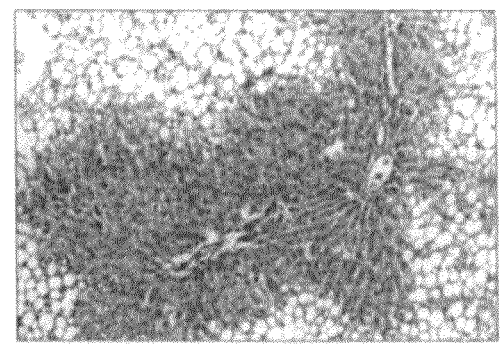
Figure 2:
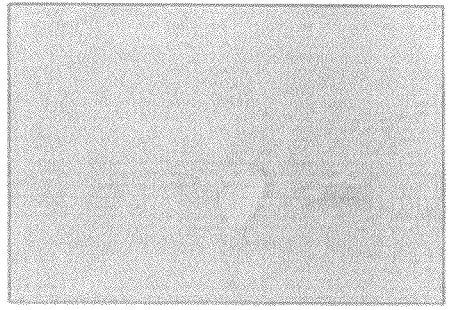
FIG. 2 shows the liver tissues stained with Sirius red in liver fibrotic rats induced by $CCl_4$ as the normal group, Model Control group, Fuzheng Huayu Preparation (Prep) I, Fuzheng Huayu Prep II, and Vitamin E group, respectively.
Figure 2:
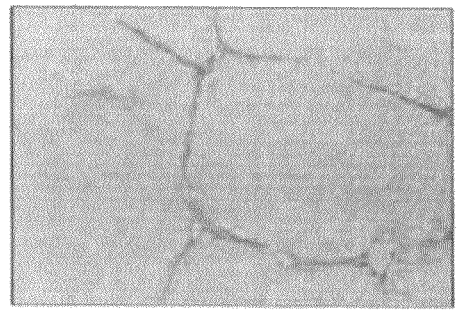
Figure 2:
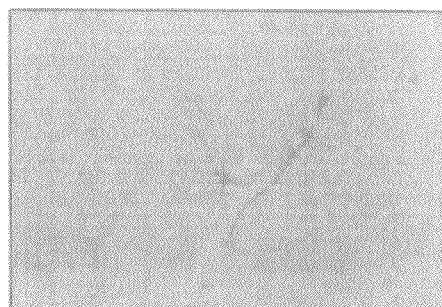
Figure 2:
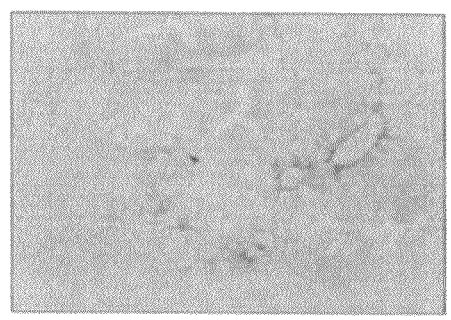
Figure 2:
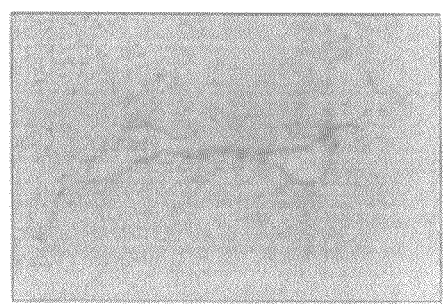
Figure 3:
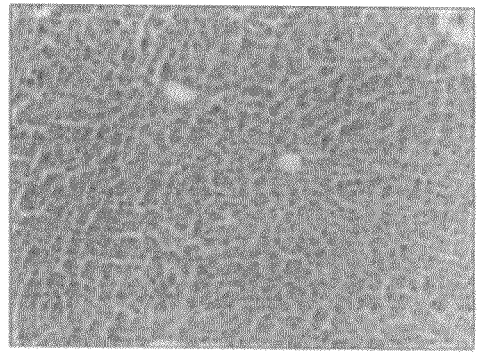
FIG. 3 shows the liver tissues stained with HE in liver fibrotic rats induced by $CCl_4$, as the normal group, Model Control group, Fuzheng Huayu Preparation (Prep) I, Fuzheng Huayu Prep II, and Vitamin E group, respectively.
Figure 3:
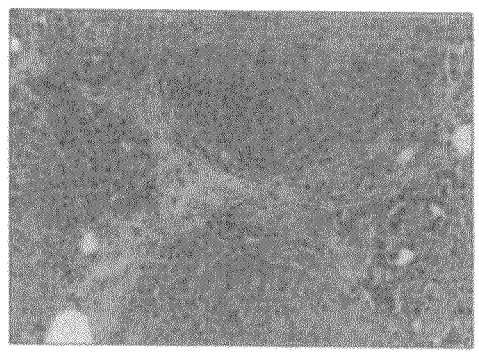
Figure 3:
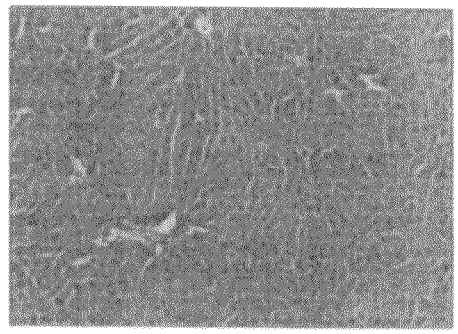
Figure 3:
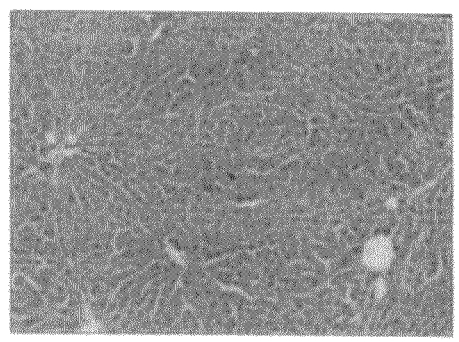
Figure 3:
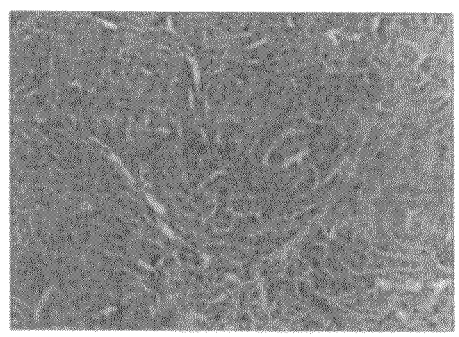

The present invention provides a composition comprising extracts from traditional Chinese medicine to treat, prevent, or ameliorate a liver disease. In some embodiments, the composition described herein comprises extracts from herbs for treating, preventing or ameliorating chronic hepatitis and liver fibrosis. In some embodiments, the invention provides a pharmaceutical formulation, which can be tablets, capsules, granules, dispersible tablets, sustained-release tablets, dropping pills or oral solutions.

As used herein, the term chronic hepatitis can be any chronic hepatitis, preferably, hepatitis B or hepatitis C.

In some embodiments, the composition described herein include an extract from *salvia miltiorrhiza* bunge; an extract from *cordyceps* extract piece; an extract from semen persicae; and an extract from at least one of *gynostemma pentaphyllum mak*, Chinese magnoliavine and pollen pini. In some embodiments, the extract from *salvia miltiorrhiza* bunge can have a percentage in the range between about 25 and about 40 wt %.

In some embodiments, the composition described herein can include an extract from *salvia miltiorrhiza* bunge in a range between about 25 and about 40 wt %, an extract from *gynostemma pentaphyllum mak* in a range between about 20 and about 35 wt %, an extract from Chinese magnoliavine in a range between about 5 and about 12 wt %, an extract from *cordyceps* extract piece in a range between about 12 and about 20 wt %, an the extract from pollen pini in a range between about 5 and 12 wt %, and an extract from semen persicae in a range between about 5 and about 12 wt %. For example, the composition can include the extract from *salvia miltiorrhiza* bunge in about 38 wt %, the extract from notoginsenosides of *gynostemma pentaphyllum mak* in about 25 wt %, the extract from Chinese magnoliavine in about 6 wt %, the extract from *cordyceps* extract piece in about 19 wt %, the extract from pollen pini in about 6 wt %, and the extract from semen persicae in about 6 wt %.

In some embodiments, the extract from *salvia miltiorrhiza* bunge can have a content of salvianolic acid 2.5-10 wt %, the extract from fructus *schisandrae chinensis* can have a content of schisandrin 0.3-2.0 wt %, the extract from *cordyceps* extract piece can have a content of adenosine 0.1 wt %-5.0 wt %, and the extract from *gynostemma pentaphyllum mak* can have a content of notoginsenosides 0.5 wt %-8.0 wt %.

In some further embodiments, the composition provided herein can further include an adjuvant, which is commonly known and used in the field of food or pharmaceuticals.

In some embodiments, the composition includes several kinds of dosages composed of several adjuvant and the extracts from traditional Chinese herbs as effective components with the weight ratio as follows:
an extract from *salvia miltiorrhiza* bunge: 25-40 wt %,
an extract from *gynostemma pentaphyllum mak*: 20-35 wt %,
an extract from Chinese magnoliavine: 5-12 wt %,
an extract from *cordyceps* extract piece: 12-20 wt %,
an extract from pollen pini: 5-12 wt %, and
an extract from semen persicae: 5-12 wt %.

In some embodiments, the weight ratio of the extracts can optionally be:
the extract from *salvia miltiorrhiza* bunge: 38 wt %,
the extract from notoginsenosides of *gynostemma pentaphyllum mak*: 25 wt %,
the extract from Chinese magnoliavine: 6 wt %,
the extract from *cordyceps* extract piece: 19 wt %,
the extract from pollen pini: 6 wt %, and
the extract from semen persicae: 6 wt %.

The composition described herein can be used to treat, prevent, or ameliorate a liver medical condition. Such liver medical condition can be a liver disease such as a chronic liver disease (e.g., chronic hepatitis and liver fibrosis). Generally, the method of treating, preventing, or ameliorating a liver medical condition includes administering to a human being a composition described herein.

Generally, the composition can be prepared as follows: weighing up *salvia miltiorrhiza* bunge, semen persicae, and *gynostemma pentaphyllum mak* according to a set or chosen ratio and then decocting them with water. The resultant liquid can be collected and combined and allowed to settle. The upper lucid is collected and then concentrated to form a wet paste. Alcohol is then added such that the total content of alcohol can reach about 70 wt % by weight. After cooling, the alcohol solution can be allowed to settle a period of time, and filtrated. The alcohol can be removed. The remaining solid is then desiccated to form a dry paste comprising extracts from *salvia miltiorrhiza* bunge, semen persicae, *gynostemma pentaphyllum mak*. On the other hand, alcohol can be added to a mixture of fermentation mycelium powder and fructus *schisandrae chinensi* and heated to reflux to form a alcohol extract of mycelium powder and fructus *schisandrae chinensi*. The alcohol extract is then cooled and collected. This alcohol extraction step can be repeated two, three or several times. The alcohol extract is then combined and filtered. Alcohol is then removed from the filtered alcohol extract. The remaining solid is dried to form a dry paste of mycelium and fructus *schisandrae chinensi*. At the same time, an amount of pollen pini can be extract with alcohol with warming (e.g., at a moderate temperature) to generate an alcohol extract of pollen pini. This extraction can be repeated two, three, or several times. The alcohol extract can be combined and concentrated to dryness to form a dry paste comprising the extract of pollen pini. The dry paste comprising extracts of, the dry paste comprising extracts of, and the dry paste comprising the extract of pollen pini can be mixed and grounded (comminuted) to form a evenly mixed composition. In some embodiments, an adjuvant such as starch can be added and mixed into the composition evenly.

In some embodiments, the present invention provides a method of making a composition described herein. In some embodiments, the method comprises
 1) providing a dry paste comprising the extracts of *salvia miltiorrhiza* bunge, semen persicae, and *gynostemma pentaphyllum mak*, which is produced by
  i) providing a mixture of *salvia miltiorrhiza* bunge, semen persicae, and *gynostemma pentaphyllum mak* according to a selected ratio,
  ii) decocting the mixture with water to generate a blend with liquid and solid parts,
  iii) allowing the liquid part to settle so as to form an upper lucid,
  iv) collecting the upper lucid, and then concentrating the upper lucid so as to form a wet paste,
  v) adding a volume of alcohol to the wet paste after cooling to form an alcohol solution so that the total content of alcohol is about 70 wt % of the solution,
  vi) allowing the alcohol solution to settle,
  vii) making filtration of the alcohol solution,
  viii) removing the alcohol to form the dry paste comprising the extracts of *salvia miltiorrhiza* bunge, semen persicae, and *gynostemma pentaphyllum mak*;

2) providing a dry paste comprising the extracts of mycelium and fructus *schisandrae chinensis*, which is produced by i) adding an amount of alcohol to a mixture of the fermentation powder of mycelium and fructus *schisandrae chinensis*, ii) heating the alcohol to reflux for a period of time to generate an alcohol extract of the fermentation powder of mycelium and fructus *schisandrae chinensis*, iii) allowing the alcohol extract to cool to ambient temperature, iv) collecting the alcohol extract of the fermentation powder of mycelium and fructus *schisandrae chinensis*, v) repeating the acts of i)-iv), vi) combining the alcohol extract generated in acts of i)-iv), vii) filtrating the alcohol extract, and viii) removing the alcohol to generate the dry paste comprising the extracts of mycelium and fructus *schisandrae chinensis*;

3) providing a dry paste comprising the extract of pollen pini, which is produced by i) extracting an amount of pollen pini with alcohol with warming to form an alcohol extract of pollen pini, ii) repeating the extracting of i), iii) combining the alcohol extract, and iv) removing the alcohol from the alcohol extract to form a dry paste comprising the extract of pollen pini;

4) mixing the dry paste comprising the extracts of *salvia miltiorrhiza* bunge, semen persicae, *gynostemma pentaphyllum mak*, the dry paste comprising the extracts of mycelium and fructus *schisandrae chinensis*, and the dry paste comprising the extract of pollen pini; and 5) grounding the dry paste comprising the extracts of *salvia miltiorrhiza* bunge, semen persicae, *gynostemma pentaphyllum mak*, the dry paste comprising the extracts of mycelium and fructus *schisandrae chinensis*, and the dry paste comprising the extract of pollen pini to form a grounded mixture of the extracts of *salvia miltiorrhiza* bunge, semen persicae, *gynostemma pentaphyllum mak*, the extracts of mycelium and fructus *schisandrae chinensis*, and the extract of pollen pini.

In some embodiments, the method can further include adding starch to grounded mixture.

The dosage forms of the invention composition can include tablets, capsules, granules, dispersible tablets, sustained-release tablets, dropping pills and/or oral solutions.

In some embodiments, the effective components of the pharmaceutical composition can be prepared as followings, which are discussed individually in detail:

1. Extract from *salvia miltiorrhiza* Bunge

Comminute the *salvia miltiorrhiza* bunge to grains, add 12 times water, extract twice at the temperature 95° C.±2° C., amalgamate the liquid on standby. It is shown that the main substances of *salvia miltiorrhiza* bunge are salvianolic acid and tanshinol sodium after measuring. The leftover of *salvia miltiorrhiza* bunge is made circumfluence with alcohol (70 wt %) twice for one hour each time. Amalgamate the liquid and concentrate it on standby. It shows that the fatty components mainly contain tanshinones after measuring. Amalgamate the concentrated liquid and dry it on standby.

The extract from *salvia miltiorrhiza* bunge is the main drug in the prescription.

2. Extract from *gynostemma pentaphyllum mak*

The extract from *gynostemma pentaphyllum mak* can be obtained after dipping it with 75 wt % alcohol and extracted with high frequency ultrasonic three times, which mainly contain notoginsenosides after measuring. The extract from *gynostemma pentaphyllum mak* can strengthen anti-pathogenic Qi in the prescription.

3. Extract from Chinese Magnoliavine

The powder of raw material of Chinese magnoliavine can be recovered after circumfluence with 80 wt % alcohol twice, drying the extracted liquid without alcohol and then comminuting. The lignin in Chinese magnoliavine which belonging to bifencyclo-octene lignin, mainly contains schisandrin. The extract efficiency reaches 0.3 wt %-2.0 wt % with 80 wt % alcohol in the process of circumfluence, which can't be reached during the common preparation, thus to influence the quality and clinical effect of the drug.

4. Extract from Cultured *cordyceps*

The dry extract which can are obtained by extracting from the raw material of cultured *cordyceps* extract piece at moderate temperature with 75 wt % alcohol three times, drying the extracted liquid without alcohol and then comminuting, mainly contains adenosine, which is one of the standard components for quality control in our invention.

5. Extract from Lipoid Substances in Pollen Pini

The dry paste, which can be obtained from pollen pini after hot circumfluence with 70 wt % alcohol and then be extracted liquid without alcohol, mainly contains flavone, which has better solubility in alcohol.

6. Extract from Semen Persicae

The effective components in semen persicae are water-soluble. In the present invention, the extract can be obtained with, for example, 10 times water decoction (twice), and then concentrated until paste, drying it on standby.

The above dry extracts can be obtained with compressing dryer and spray dryer.

After measuring with HPLC, the extract from *salvia miltiorrhiza* bunge contains salvianolic acid with content 2.5 wt %-10 wt %, the extract from fructus *schisandrae chinensis* contains schisandrin with content 0.3 wt %-2.0 wt %, the extract from *cordyceps* extract piece contains adenosine with content 0.1 wt %-5.0 wt %. After measuring with colorimetry, the extract from *gynostemma pentaphyllum mak* contains notoginsenosides with content 0.5 wt %-8.0 wt %.

A few examples of the dosage forms of the composition described herein can be prepared according to the method described below.

The above dry extracts in a chosen ratio can be mixed evenly after comminuting separately and then added into a quantity of adjuvant. The blend is then mixed evenly, formulated into grains, dried, pressed, coated, forming tablets.

The above dry extracts in a chosen ratio can be mixed evenly after comminuting separately, and added into certain quantity of adjuvant, at last put them into capsule.

The above dry extracts in a chosen ratio can be added an amount of adjuvant. The mixture can then be dried, and formulated into grains, forming granules.

The dry extracts described herein in a chosen ratio can be mixed evenly after comminuting separately and then added into certain quantity of adjuvant. The mixture can then be formulated into grains, and dried to form tablets. Dispersed tablets can be therefore obtained.

The dry extracts described in a chosen ratio can be mixed evenly after comminuting separately and then added into certain quantity of adjuvant. The mixture can then be formulated into to grains. The grains can then be dried, generating tablets. In some embodiments, the tablets can include a material that causes the tablet to have sustained-release properties.

The dry extracts described herein in a chosen ratio can be mixed evenly after comminuting separately and then added into certain quantity of adjuvant and solvent. The mixture can then be heated to melting to generate the dropping pills after dropping.

In some embodiments, the dry extracts described in a chosen ratio herein can be dissolved with about 1/3 water. Adjuvant and water can be added to the mixture. The resultant solution/liquid can be filtered and loaded to generate an oral solution of the composition described herein.

The quality of the medicinal materials accords with the regulations of Chinese pharmacopoeia of 2005 edition. The herbal materials are described as follows:

Semen persicae is the dry mature seed of *prunus persica* (L.) batsch or *prunus davidiana* (carr.) franch;

*Salvia miltiorrhiza* bunge is the dry root or rhizome of *salvia miltiorrhiza* bge;

Fructus *schisandrae chinensis* is the dry mature fruit of schisandra chinensis (turcz.) baill or *schisandra sphenanthera* rehd.et wits;

*Gynostemma pentaphyllum mak* is the dry part overground of *gynostemma pentaphyllam* (thumb) mak;

Fermentation mycelium powder is obtained by fermentation of *paccilomyces hepialid* chen Cs-4 from *cordyceps sinensis* (berks acc) after filtrating and drying the product;

Pollen pini is the dry pollen of *pinus tabulaeformis* from *pinus massoniana*.

The compositions described herein can be formulated into any desirable dosage forms. In some embodiments, the composition can be formulated into tablets.

To show the effectiveness against liver fibrosis, a study was conducted to show the comparative effect against liver fibrosis and peroxidation injury in liver were conducted between the invention (named as Fuzheng Huayu Prep I) and already existing capsule dosage (named as Fuzheng Huayu Prep II). The result shows that our invention (Prep I) has the better effect than existing capsule (Prep II). The Fuzheng Huayu Prep I composed of extracts from Chinese plants and herbs has the effect of activating blood and resolving stasis as well as invigorating energy and nourishing the liver. The effect of treating hepatitis B and hepatic fibrosis has also been improved.

EXAMPLES

Example 1

The dry extracts in a chosen ratio as described above were mixed evenly after comminuting separately and then added into certain quantity of adjuvant. They were then mixed evenly to form grains, dried, pressed and coated. The ratio between drugs and the adjuvant is as followings: the mixed dry extracts 60.0 wt %-80.0 wt %, pregelatinized starch 15 wt %-20 wt %, microcrystalline cellulose 3 wt %-10 wt %, sodium carboxymethyl starch 2 wt %-10 wt %, magnesium stearate 0.1 wt %-0.4 wt %.

Example 2

The above dry extracts were mixed evenly after comminuting separately and then added into certain quantity of adjuvant. The mixture was then formulated into capsules. The ratio between the extracts and the adjuvant can be as follows: the mixed dry extracts 65 wt %-85 wt %, microcrystalline cellulose 0 wt %-35 wt %, calcium sulfate 0 wt %-5 wt %.

Example 3

The above dry extracts were mixed evenly after comminuting separately and then added into certain quantity of adjuvant, namely dextrin. The ratio between drugs and the adjuvant is as follow: the mixed dry extracts 60 wt %-90 wt %, dextrin 40 wt %-10 wt %. The mixture was then mixed evenly, formulated into granules, dried at the temperature of 60-65° C., and griddled to form the granules.

Example 4

The above dry extracts were mixed evenly after comminuting separately, formulated into tablets after adding adjuvant and disintegrant. As an alternative, they could be made into tablets with powder directly. The ratio between drugs and the adjuvant is as followings: the mixed dry extracts 10 wt %-25 wt %, sodium carboxymethyl starch 5 wt %-80 wt %, guar gum 0 wt %-20 wt %, Siberia cocklebur gum 0 wt %-25 wt %, sodium alginate 0 wt %-20 wt %. The mixture was made into tablets after granulation or with powder directly.

Example 5

The above dry extracts were mixed evenly after comminuting separately and made tablets after adding adjuvant. The ratio between drugs and the adjuvant is as followings: the mixed dry extracts 10 wt %-25 wt %, citric acid 2 wt %-10 wt %, hydroxypropyl methyl cellulose 50 wt %-60 wt %, magnesium stearate 0.3 wt %-1.0 wt %. The extracts and hydroxypropyl methyl cellulose were mixed together, made into a soft material with citric acid dissolving in alcohol, and then made into granules, dried, griddled and made into tablets after mixing with magnesium stearate.

Example 6

The above dry extracts were mixed evenly after comminuting separately, make dropping pills in a common way after adding adjuvant. The ratio between drugs and the adjuvant is as followings: the mixed dry extracts 8 wt %-15 wt %, PEG6000 11 wt %-85 wt %, polysorbate 0.0 wt %-1.0 wt %, The above substances were heated up to 150° C. or so in oil until melting. The dropping temperature was almost 85° C. with the rate of dropping 20-35 pills/minute and the dimethiconum as the condensate.

Example 7

The above dry extracts were dissolved with 1/3 water and added into some quantity of adjuvant and then made into oral solutions in a common way. The adjuvant is as followings: rectifying agent such as steviostde 0.2 wt %-1.0 wt %, solubilizing agent such as tween 80 0.5 wt %-2.0 wt %. The mixture was added into water, filtrated and loaded.

Example 8

Pharmacological Action Experiment (1) Prophylaxis Action on Liver Fibrosis

Pharmacological model: The liver fibrosis model in rat was induced by hypodermical injection of $CCl_4$ and fed with the food containing high lipid and low protein. 100 wt % $CCl_4$ was used at the first injection with a dosage of 1 ml/kg wt rat, then 40 wt % $CCl_4$ in olive oil with a dosage of 3 ml/kg wt. was applied, twice per week and lasting for 2 weeks. During the first 2 weeks of intoxication, the rats were fed with the food containing 79.5 wt % maizena, 20 wt % grease and 0.5 wt % cholesterol, then with the pure maize food for later 4 weeks.

Models grouping and drug administration: the model rats were divided into model control, Fuzhenghuayu Prep I, Recipe Fuzhenghuayu Prep II and Vitamin E group, while the normal rats were normal control, with total 5 groups. Fuzhenghuayu Prep I and II group orally took with Fuzhenghuayu Prep I and II respectively at the dose of 4.6 g/kg, Vitamin E group received 50 mg/kg of VitE, The drugs were administrated once every day for 6 weeks. All dosages were 10 times human dosage with 65 kg by the same body weight.

Pharmacodynamic function: The liver tissue pathological examination show Fuzhenghuayu Prep I, Fuzhenghuayu Prep II could obviously attenuate hepatic inflammation and collagen deposition in the fibrotic model rat livers. According to well recognized standards of grading and staging for evaluation of liver inflammation and fibrosis, we found that all above 3 drugs could decrease liver fibrosis staging score, and Fuzhenghuayu Prep I had the best action among them. FIG. 1 showed the effect of different Fuzhenghuayu Preps on rat liver fibrosis stages induced by $CCl_4$.

Serum and liver tissue biochemical examinations showed that Fuzhenghuayu Prep I and Fuzhenghuayu Prep II could improve the serum liver function parameters obviously in model rats, decreased hepatic collagen level (Hyp content), and decreased the contents of triglyceride (TG) and malondialdehyde (MDA), superoxide dismutase (SOD) activity significantly. There are no obvious difference between Fuzhenghuayu Preps and VitE. These indicated that both Fuzhenghuayu Prep I and II have good actions against liver fibrosis and lipid peroxidation. Compared to Fuzhenghuayu Prep II, Fuzhenghuayu Prep I have a better effect on lowering ALT level, hepatic collagen content, TAG and MDA content. Table 2 expressed the effect of different Fuzhenghuayu Preps on the serum liver function parameters in fibrotic rats induced by $CCl_4$. Table 3 expressed the effect of different Fuzhenghuayu Preps on hepatic Hyp, TAG, MAD contents and SOD activity in fibrotic rats induced by $CCl_4$ (x±s).

The results were shown in Tables 1-6.

TABLE 1

Different Preparations of Fuzhenghuayu Decoction on Liver Fibrotic Stages in $CCl_4$ Induced Fibrotic Rats

| Group | n | S0 | S1 | S2 | S3 | S4 | R |
|---|---|---|---|---|---|---|---|
| Normal | 10 | 10 | 0 | 0 | 0 | 0 | 0.079 |
| Model | 14 | 0 | 0 | 3 | 9 | 2 | 0.819* |
| Prep I | 13 | 0 | 7 | 5 | 1 | 0 | 0.457# |
| Prep II | 12 | 0 | 5 | 5 | 2 | 0 | 0.516# |
| Vit E | 14 | 0 | 6 | 6 | 2 | 0 | 0.506# |

Ridit examination, *$P < 0.01$, vs. Normal; #$P < 0.01$, vs. Control.

TABLE 2

Different Preparations of Fuzhenghuayu Decoction on Serum Liver Function in $CCl_4$ Induced Liver Fibrotic Rats (x ± s)

| Group | n | ALT (U/L) | AST (U/L) | T. BIL (μmol/L) | T. Protein (g/L) | Alb (g/L) |
|---|---|---|---|---|---|---|
| Normal | 10 | 37.7 ± 13.2 | 101.4 ± 15.0 | 11.3 ± 2.7 | 55.3 ± 3.9 | 29.3 ± 1.1 |
| Control | 14 | 182.1 ± 67.5* | 190.1 ± 55.0 | 18.9 ± 6.1* | 55.2 ± 2.0 | 26.1 ± 1.3 |
| Prep I | 13 | 104.3 ± 41.8#,Δ | 164.6 ± 25.9 | 13.6 ± 4.1# | 53.4 ± 3.3 | 27.1 ± 1.7 |
| Prep II | 12 | 140.6 ± 34# | 169.5 ± 29.0 | 14.9 ± 3.2# | 51.2 ± 2.6 | 27.0 ± 2.1 |
| Vit E | 13 | 106.4 ± 45.9# | 127.7 ± 37.2 | 14.1 ± 3.3# | 55.8 ± 4.2 | 27.7 ± 1.1 |

*$P < 0.01$, vs. Normal; #$P < 0.01$, vs. Control; Δ$P < 0.05$, vs. Prep II.

TABLE 3

Different Preparations of Fuzhenghuayu Decoction on Hepatic Hyp, Triglyceride, MDA and SOD in $CCl_4$ Induced Fibrotic Rats (x ± s)

| Groups | n | Hyp (μg/g liver) | Triglyceride (μg/g liver) | MDA (μmol/g protien) | SOD (NU/g liver) |
|---|---|---|---|---|---|
| Normal | 10 | 239.7 ± 39.9 | 6.1 ± 0.8 | 5.7 ± 1.4 | 852.5 ± 58.5 |
| Control | 14 | 408.1 ± 63.2* | 15.1 ± 2.6* | 21.5 ± 5.7* | 716.7 ± 158.5* |
| Prep I | 13 | 264.1 ± 32.5#,Δ | 10.5 ± 3.1#,Δ | 7.8 ± 1.5#,Δ | 872.9 ± 116.7# |
| Prep II | 12 | 306.9 ± 48.5# | 12.9 ± 2.1# | 11.3 ± 2.8# | 852.5 ± 69# |
| Vit E | 13 | 296.2 ± 49.8# | 12.6 ± 3.7# | 4.5 ± 1.3# | 1062 ± 83# |

*$P < 0.01$, vs. Normal; #$P < 0.01$, vs. Control; Δ$P < 0.05$, vs. Prep II.

(2) The Treatment Effect of Fuzheng Huayu Preps on the Hepatic Fibrosis in Rats Induced by (Dimethylnitrosamine, DMN).

Pharmacological model: The hepatic fibrosis model was induced by intraperitoneal injections of dimethylnitrosamine at a dosage of 1 μg/kg rat wt, the injection was given on the first consecutive 3 days of each week over a period of 4 weeks, once per day.

Groups and drug administration: After establishing the model, the model rats were divided into model control, Fuzheng Huayu Prep I, Fuzheng Huayu Prep II, and (N-Acetylcysteine, NAC) groups, also normal rats was set as the normal control, with total 5 groups. The model rats in Fuzheng Huayu Prep I and II took orally Fuzheng Huayu decoction at the dosage of 4.6 g/kg rat wt from the beginning of the 5th week to end of the 8$^{th}$ week, one time per day for 4 weeks, NAC group received NAC at the dosage of 100 mg/kg wt, and controls took the same volume of saline. (body weight equivalent to 10 times of 65 kg adult dosage).

Pharmacodynamic effect: After the treatment of Fuzheng Huayu prep I and II, the histological pathological examination showed that the inflammation and collagen deposition alleviated obviously in model rats, and the hepatic fibrosis staging obviously decreased. There were no significant difference between Fuzheng Huayu Preps and NAC treated groups. However, Fuzheng Huayu Prep I group had better action than group II.

Figure 4:
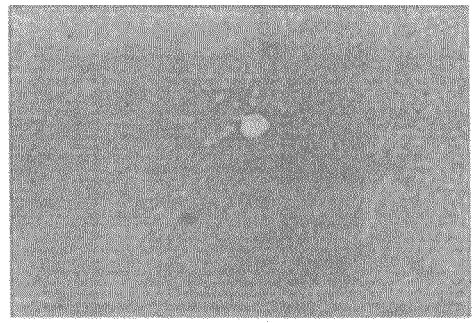
FIG. 4 shows the liver tissues stained with Sirius red in liver fibrotic rats induced by $CCl_4$ as the normal group, control group, Fuzheng Huayu Preparation (Prep) I, Fuzheng Huayu Prep II, and Vitamin E group, respectively. In the figure, liver tissue were stained with Sirius red, there were fewer collagens deposition only in the portal and central vein area in the normal group. In the control group, collagen accumulated obviously, along the degenerated hepatocytes, and formed fibrous septa. The model rats prevented with Fezheng Huayu Preps or Vitamin E had much better conditions of hepatic inflammation compared to the controls.
Figure 4:
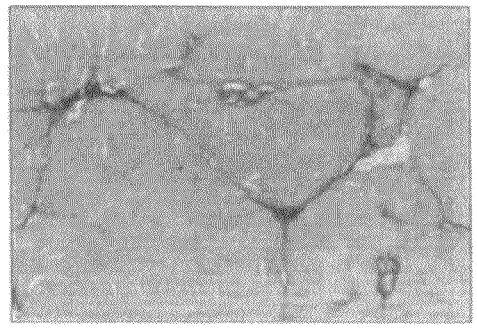
Figure 4:
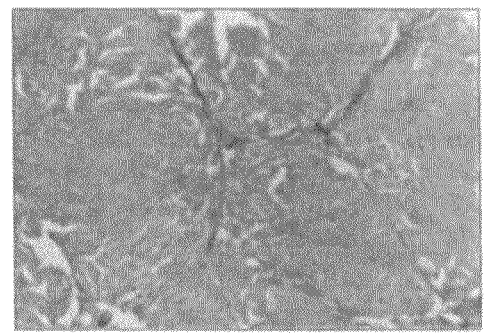
Figure 4:
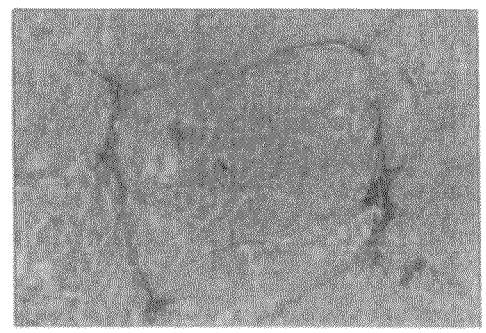
Figure 4:
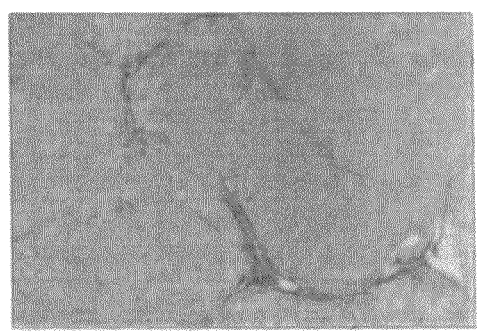

FIG. 4 shows the different influence of hepatic fibrosis staging in the two different Fuzheng Huayu preparations (Preps).

The serum and liver tissue biochemical examination revealed that both Fuzheng Huayu Prep I and II could obviously decrease serum ALT activity, total bilirubin level, increased serum Alb content, reduce hepatic collagen content, and improve SOD activity. It is indicated that Fuzheng Huayu Preps had good effects for treating experimental hepatic fibrosis. Compared to Fuzheng Huayu Prep II, Fuzheng Huayu Prep I had much better action on decreasing the collagen content and improving SOD activity.

TABLE 4

Different Preparations of Fuzhenghuayu Decoction on Liver Fibrotic Stages in DMN Induced Fibrotic Rats (x ± s)

| Groups | n | S0 | S1 | S2 | S3 | S4 | R |
|---|---|---|---|---|---|---|---|
| Normal | 7 | 7 | 0 | 0 | 0 | 0 | 0.083 |
| Control | 7 | 0 | 0 | 1 | 2 | 4 | 0.772* |
| Prep I | 8 | 0 | 1 | 5 | 1 | 1 | 0.364# |
| Prep II | 8 | 0 | 1 | 3 | 3 | 1 | 0.436# |
| NAC | 12 | 0 | 1 | 5 | 4 | 2 | 0.415# |

Ridit examination, *P < 0.01, vs. Normal; #P < 0.01, vs. Control.

TABLE 5

Different Preparations of Fuzhenghuayu Decoction on Serum Liver Function in DMN Induced Fibrotic Rats (x ± s)

| Group | n | ALT (U/L) | AST (U/L) | T. BIL (μmol/L) | T. Protein (U/L) | Alb (U/L) |
|---|---|---|---|---|---|---|
| Normal | 1 | 33.1 ± 111.4 | 54.9 ± 18.2 | 15.5 ± 1.2 | 60.1 ± 16.9 | 32.4 ± 1.7 |
| Control | 1 | 101.6 ± 22.2* | 95.9 ± 22.2 | 17.1 ± 3.2 | 52.4 ± 10.9 | 24.7 ± 1.9* |
| Prep I | 8 | 78.8 ± 14.3# | 87.8 ± 10.7 | 16.6 ± 1.5 | 54.4 ± 10.5 | 29.1 ± 4.8# |
| Prep II | 8 | 80.2 ± 11.8# | 85.8 ± 12.2 | 16.9 ± 3.2 | 54.1 ± 12.5 | 28.3 ± 4.4 |
| NAC | 10 | 67.7 ± 36.1# | 76.5 ± 25.5 | 18.8 ± 2.8 | 60.4 ± 11.21 | 30.9 ± 5.5# |

*P < 0.01, vs. Normal; #P < 0.01, vs. Control.

TABLE 6

Different Preparations of Fuzhenghuayu Decoction on Hepatic Hyp content and SOD activity in DMN Induced Fibrotic Rats (x ± s)

| Group | n | Hyp (μg/g liver) | SOD($10^3$ × NU/g protein) |
|---|---|---|---|
| Normal | 7 | 225.7 ± 20.6 | 237.2 ± 43.4 |
| Control | 7 | 614.6 ± 100.3* | 181.8 ± 21.2* |
| Prep I | 8 | 434.7 ± 38.4#,Δ | 286.8 ± 25.7#,Δ |
| Prep II | 8 | 485.9 ± 151.2# | 258.5 ± 51.2# |
| NAC | 10 | 482.1 ± 124.4# | 252.2 ± 47.6# |

*P < 0.01, vs. Normal; #P < 0.01, vs. Control; ΔP < 0.05, vs. Prep II.

Compared to already exiting preparation, the invent has better actions on preventing, treating, or ameliorating liver fibrosis, protecting liver inflammation; in particular it has advantages in treating liver fibrosis and protecting hepatic peroxidation.

The invention claimed is:

1. A composition for treating or ameliorating hepatic fibrosis caused by a liver disease, comprising
   an extract from *salvia miltiorrhiza* bunge comprising 2.5-10 wt % of salvianolic acid and tanshinones;
   an extract from *cordyceps* extract piece comprising 0.1-5.0 wt % adenosine;
   an extract from Chinese magnoliavine comprising 0.3-2.0 wt % schisandrin;
   an extract from gynostemma *pentaphyllum mak* comprising 0.5-8.0 wt % notoginsenosides; and
   an extract from at least one of pollen pini and semen persicae;
wherein
   the extract from *salvia miltiorrhiza* bunge is between 25 and 40 wt %;
   the extract from *cordyceps* extract piece is between 12 and 20 wt %;
   the extract from Chinese magnoliavine is between 5 and 12 wt %;
   the extract from gynostemma *pentaphyllum mak* is between 20 and 35 wt %;
wherein the composition is prepared by a method comprising the following steps:
   (1) obtaining the extract from *salvia miltiorrhiza* bunge by comminuting *salvia miltiorrhiza* bunge to grains,
      adding 12 times water,
      extracting the comminuted *salvia miltiorrhiza* bunge with water twice at the temperature 95° C.±2° C., amalgamating the liquids, and concentrating the extract;
      extracting the leftover of *salvia miltiorrhiza* bunge with 70 wt % alcohol twice, amalgamating the liquids, and concentrating the extract,
      combining the concentrated extracts and drying;
   (2) obtaining the extract from *gynostemma pentaphyllum mak* by dipping *gynostemma pentaphyllum mak* in 75 wt % alcohol and extracting with high frequency ultrasonic 3 times, and concentrating and drying the extract;
   (3) obtaining the extract from Chinese magnoliavine by extracting powder of raw material of Chinese magnoliavine by circumfluence with 80 wt % hot alcohol twice, and concentrating and drying the extract;
   (4) obtaining the extract from cultured *cordyceps* extract piece by extracting the raw material of cultured *cordyceps* extract piece with 75 wt % alcohol three times, and concentrating and drying the extract;

(5) obtaining the extract from at least one of pollen pini and semen persicae; wherein
the extract from pollen *pini* is obtained by circumfluence with 70 wt % hot alcohol, and concentrating and drying the extract;
the extract from semen *persicae* is obtained by extracting semen *persicae* with 10 times water, and concentrating and drying the extract;
and
(6) combining the dried extracts and mixing them evenly.

2. The composition of claim 1, comprising:
an extract from pollen pini at between 5 and 12 wt %.

3. The composition of claim 1, comprising:
an extract from semen persicae at between 5 and 12 wt %.

4. The composition of claim 1, comprising:
an extract from pollen pini at between 5 and 12 wt %; and
an extract from semen persicae at between 5 and 12 wt %.

5. The composition of claim 1, consisting of:
the extract from *salvia miltiorrhiza* bunge at 38 wt %;
the extract from *cordyceps* extract piece at 19 wt %,
the extract from Chinese magnoliavine at 6 wt %,
the extract from *gynostemma pentaphyllum mak* at 25 wt %,
the extract from pollen pini at 6 wt %, and
the extract from semen persicae at 6 wt %.

6. The composition of claim 1, further comprising:
an adjuvant.

7. The composition of claim 6, wherein the adjuvant is selected from the group consisting of starch, cellulose, stearate, sulfate, dextrin, guar gum, Siberia cocklebur gum, alginate, citric acid, polyethylene glycol (PEG), polysorbate, steviostde, and tween.

8. The composition of claim 1, further comprising:
a disintegrant.

9. The composition of claim 1, further comprising:
an adjuvant and a disintegrant.

10. The composition of claim 1 in a formulation selected from tablets, capsules, granules, dispersible tablets, sustained-release tablets, dropping pills or oral solutions.

11. The composition of claim 1, wherein the liver disease is chronic hepatitis.

12. The composition of claim 11, wherein the chronic hepatitis is hepatitis B or hepatitis C.

13. A method of treating or ameliorating hepatic fibrosis caused by a liver disease, comprising:
administering to a human subject an effective amount of the composition of claim 1.

14. The method of claim 13, wherein the liver disease is chronic hepatitis.

15. The method of claim 14, wherein the chronic hepatitis is hepatitis B or hepatitis C.

16. A method of preparing a composition comprising
an extract from *salvia miltiorrhiza* bunge comprising 2.5-10 wt % of salvianolic acid and tanshinones;
an extract from *cordyceps* extract piece comprising 0.1-5.0 wt % adenosine;
an extract from Chinese magnoliavine comprising 0.3-2.0 wt % schisandrin;
an extract from *gynostemma pentaphyllum mak* comprising 0.5-8.0 wt % notoginsenosides; and
an extract from at least one of pollen pini and semen persicae;
wherein the method comprising the following steps:
(1) obtaining the extract from *salvia miltiorrhiza* bunge by comminuting *salvia miltiorrhiza* bunge to grains,
adding 12 times water,
extracting the comminuted *salvia miltiorrhiza* bunge with water twice at the temperature 95° C.±2° C., amalgamating the liquids, and concentrating the extract;
extracting the leftover of *salvia miltiorrhiza* bunge with 70 wt % alcohol twice, amalgamating the liquids, and concentrating the extract,
combining the concentrated extracts and drying;
(2) obtaining the extract from *gynostemma pentaphyllum mak* by dipping *gynostemma pentaphyllum mak* in 75 wt % alcohol and extracting with high frequency ultrasonic 3 times, and concentrating and drying the extract;
(3) obtaining the extract from Chinese magnoliavine by extracting powder of raw material of Chinese magnoliavine with 80 wt % alcohol twice via circumfluence, and concentrating and drying the extract;
(4) obtaining the extract from cultured *cordyceps* extract piece by extracting the raw material of cultured *cordyceps* extract piece with 75 wt % alcohol three times, and concentrating and drying the extract;
(5) obtaining the extract from at least one of pollen pini and semen persicae; wherein
the extract from pollen pini is obtained by circumfluence with 70 wt % hot alcohol, and concentrating and drying the extract;
the extract from semen persicae is obtained by extracting semen persicae with 10 times water, and concentrating and drying the extract;
and
(6) combining the dried extracts and mixing them evenly.

17. The method of claim 16, wherein
the extract from *salvia miltiorrhiza* bunge is between 25 and 40 wt %;
the extract from *cordyceps* extract piece is between 12 and 20 wt %;
the extract from Chinese magnoliavine is between 5 and 12 wt %; and
the extract from *gynostemma pentaphyllum mak* is between 20 and 35 wt %.

18. The method of claim 16, further comprising adding an adjuvant, a disintegrant, or a combination thereof to the mixture of the dried extracts.

\* \* \* \* \*